United States Patent [19]

Dorner et al.

[11] Patent Number: 6,027,724

[45] Date of Patent: Feb. 22, 2000

[54] NON-TOXIGENIC STRAIN OF *ASPERGILLUS ORYZAE* AND *ASPERGILLUS SOJAE* FOR BIOCONTROL OF TOXIGENIC FUNGI

[75] Inventors: Joe W. Dorner; Bruce W. Horn; Richard J. Cole, all of Albany, Ga.

[73] Assignee: The United States of America, as represented by the Secretary of Agriculture, Washington, D.C.

[21] Appl. No.: 09/110,132

[22] Filed: Jul. 6, 1998

[51] Int. Cl.[7] .......................... A01N 25/00; A01N 25/32; A01N 63/00; C12N 1/14; D06M 16/00
[52] U.S. Cl. .......................... 424/93.5; 424/405; 424/406; 435/256.1; 435/264; 435/800; 435/911; 435/913; 435/915; 435/918
[58] Field of Search ..................... 424/93.5, 405, 424/406; 435/256.1, 264, 800, 911, 913, 915, 918

[56] References Cited

U.S. PATENT DOCUMENTS

| | | | |
|---|---|---|---|
| 5,171,686 | 12/1992 | Coty | 435/254 |
| 5,292,661 | 3/1994 | Cole et al. | 435/267 |
| 5,294,442 | 3/1994 | Coty | 424/93 |

OTHER PUBLICATIONS

Horn et al., *Mycologia*, vol. 88(4), pp. 574–587, 1996.
Dorner et al., *Mycopathologia*, vol. 87, pp. 13–15, 1984.
Dorner et al., *Journal of Food Protection*, vol. 55(11), pp. 888–892, 1992.
Gupta et al, "Reg. of Aflatox. Biosyn. Pt. 3 Comp. Study . . . ", Microbios 19 (75). 1977—See Abstr. Only.

*Primary Examiner*—David M. Naff
*Assistant Examiner*—Deborah K. Ware
*Attorney, Agent, or Firm*—M. Howard Silverstein; John D. Fado; Gail E. Poulos

[57] ABSTRACT

Non-toxigenic strains of Aspergillus such as from the species *Aspirgillus oryzae* and *Aspergillus sojae* are useful fungal biocontrol agents for preventing toxin contamination in agricultural commodities, especially those for human consumption such as peanuts and corn. These strains do not produce aflatoxin, any bis-furan ring-containing intermediates of the aflatoxin biosynthetic pathway and cyclopiazonic acid. They are also useful for controlling toxin damage to crops such as cotton. The strains include Aspergillus strains NRRL 21368, NRRL 21369, NRRL 21882, NRRL 30038, NRRL 30039 and mixtures thereof.

8 Claims, No Drawings

NON-TOXIGENIC STRAIN OF ASPERGILLUS ORYZAE AND ASPERGILLUS SOJAE FOR BIOCONTROL OF TOXIGENIC FUNGI

BACKGROUND OF THE INVENTION

1. Field of the Invention

The present invention relates to novel non-toxigenic strains of Aspergillus including *Aspergillus flavus* (*A. flavus*), *Aspergillus parasiticus* (*A. parasiticus*), *Aspergillus oryzae* (*A. oryzae*), and *Aspergillus sojae* (*A. sojae*); agricultural compositions containing non-toxigenic strains of *Aspergillus flavus* (*A. flavus*), *Aspergillus parasiticus* (*A. parasiticus*), *Aspergillus oryzae* (*A. oryzae*), and *Aspergillus sojae* (*A. sojae*) on agriculturally acceptable carriers; and to methods for the control of toxin contamination in agricultural commodities using non-toxigenic strains of *A. flavus*, *A. parasiticus*, *A. oryzae*, and *A. sojae*.

2. Description of the Related Art

Aflatoxins are potent hepatotoxic, carcinogenic compounds produced by *A. flavus* Link:Fr. and *A. parasiticus* Speare (CAST, In: Mycotoxins: Economic and Health Risks. Report 116, 99 pp., Council for Agricultural Science and Technology, 137 Lynn Avenue, Ames, IA 50010). Cyclopiazonic acid (CPA) is another potent mycotoxin that is produced by *A. flavus*, but not by *A. parasiticus*. When these fungi invade and grow in commodities such as peanuts, corn, cottonseed, and tree nuts, the resulting contamination with the aflatoxins and CPA often makes the commodity unfit for consumption. The United States peanut industry has identified aflatoxin contamination of peanuts as the number one problem for which a solution is needed (Consensus Report of the National Peanut Council Quality Task Force, 1987, National Peanut Council, Alexandria, Va. 22314). Because peanuts are used primarily for food, strict regulatory limits for the amount of aflatoxin allowable in finished peanut products have been established. Although the United States Food and Drug Administration has an action level of 20 ppb of total aflatoxins in food products, international tolerances for aflatoxin are much lower, typically in the range of 0–4 ppb, and are important because U.S. companies compete internationally in the market to export peanuts and peanut products. For this reason the United States peanut industry has a goal to ensure the delivery of aflatoxin-free peanut products by the year 2000. Although aflatoxin contamination of peanuts can occur during postharvest curing and storage, the most significant contamination usually occurs prior to harvest during periods of late-season drought stress as peanuts are maturing. The only known method for controlling preharvest aflatoxin contamination in peanuts is irrigation, an option that is unavailable to the majority of peanut growers.

Cyclopiazonic acid is an indole-tetramic acid that was first isolated from cultures of *Penicillium cyclopium* Westling in 1968 (Holzapfel, Tetrahedrom, Volume 24, 2101–2119, 1968). CPA is now know to be produced by a variety of fungi including *P. patulum*, *P. viridicatum*, *P. puberulum*, *P. crustosum*, *P. camemberti*, *A. flavus*, *A. versicolor* and *A. oryzae*. In addition, CPA has been found as a natural contaminant of corn and peanuts, often occurring together with aflatoxin (Lansden and Davidson, Applied and Environmental Microbiology, Volume 45, 766–769,1983; Urano et al., Journal of AOAC International, Volume 75, 838–841, 1992). It was also implicated as the causative agent in a human intoxication involving consumption of contaminated millet (Rao and Husain, Mycopathologia, Volume 89, 177–180, 1985). With the discovery of CPA production by *A. flavus*, 54 isolates of *A. flavus* were investigated for production of CPA and aflatoxin (Gallagher et al., Mycopathologia, Volume 66, 31–36, 1978). It was found that 28 of the 54 (52%) produced CPA whereas only 18 (33%) produced aflatoxin. Regulatory limits for CPA have not been established; however, because of the co-occurrence of aflatoxin and CPA in commodities, efforts to attain biological control of aflatoxin also need to attain control of CPA.

It has been previously found that co-cultivation of either *A. parasiticus* or *A. flavus* with species of Penicillium reduce levels of aflatoxin production while co-cultivation of Fusarium species had no such effect (Ehrlich et al., Experiential, Volume 41, 691–693, 1985). These tests did not involve the use of a soil environment. Co-cultivation with *A. niger* completely eliminated the production of aflatoxin by a culture of *A. flavus* (Wicklow et al., Phytopathology, Volume 70, 761–764, 1980). This testing was done under laboratory controlled conditions in which the food source involved sterilized corn.

Cotty (U.S. Pat. No. 5,171,86 Dec. 15, 1992 and U.S. Pat. No. 5,294,442 Mar. 15, 1994) discloses a non-toxigenic strain of *A. flavus* which inhibits aflatoxin production by toxigenic strains. The patent teaches that agricultural commodities inoculated simultaneously with both a non-toxigenic strain and a toxigenic strain produce seed with up to 100-fold less aflatoxin than commodities inoculated with a toxigenic strain alone. The patent only discloses that the patented strain fails to produce aflatoxin. There is no disclosure of its lack of ability to produce other toxins such as, for example, CPA.

Cole et al.(U.S. Pat. No. 5,292,661 Mar. 8, 1994) and Dorner et al.(Journal of Food Protection, Volume 55, 888–892, 1992) disclose a non-aflatoxigenic strain of *A. parasiticus*. The references teach the use of this strain as a biocontrol agent which reduces aflatoxin contamination of soil-borne crops.

Tantaoui-Elaraki (Journal of Environmental Pathology, Toxicology and Oncology, Volume 11 (2), 97–101, 1992), Lemke et al. (Applied and Environmental Microbiology, July, 1989, 1808–1810), Jishen et al. (Acta Academiae Medicinae, Volume 8, (1),70–71, February 1986), and Lee (Mycopathologia, Volume 107, 127–130, 1989), all disclose non-toxigenic strains of *A. flavus* wherein the strains do not produce aflatoxin.

Horn et al. (Mycologia, Volume 88 (4), 574–587, 1996) discloses isolates of *A. flavus* that fail to produce the mycotoxins CPA and aflatoxin.

While various strains of non-toxigenic Aspergillus for control of toxigenic fungi are known in the art, there still remains a need for an effective biocontrol agent for toxigenic fungi. The present invention described below includes non-toxigenic strains of Aspergillus, especially non-toxigenic strains of *A. flavus*, *A. parasiticus*, *A. oryzae*, and *A. sojae*, which are antagonistic to toxigenic fungi. The present invention also provides a method for controlling toxigenic fungi in agricultural crops which is different from the related art biocontrol agents.

SUMMARY OF THE INVENTION

It is, therefore, an object of the present invention to provide biocontrol agents for the control of toxigenic fungi in plants.

Another object of the present invention is to provide non-toxigenic fungi which are biocontrol agents for preventing contamination of crops with toxin-producing fungi.

It is another object of the present invention to provide non-toxigenic strains of fungi selected from *A. flavus, A. parasiticus, A. oryzae,* and *A. sojae* as biocontrol agents for preventing contamination of crops with toxin-producing fungi.

A further object of the present invention is to provide an agricultural biocontrol composition containing at least one non-toxigenic strain of Aspergill us, especially *A. flavus, A. parasiticus, A. oryzae,* and *A. sojae.*

A still further object of the present invention is to provide a method for biocontrol of toxin-producing fungi in plants.

Another object of the present invention is to provide a method for biocontrol of toxin-producing fungi in plants which includes applying non-toxigenic strains of fungi to the soil.

A further object of the present invention is to provide a biocontrol method for peanuts, corn and cotton, which includes applying non-toxigenic strains selected from *A. flavus, A. parasiticus, A. oryzae,* and *A. sojae* and mixtures thereof that do not produce aflatoxin or CPA, to the soil.

Further objects and advantages of the present invention will become apparent from the following description.

DEPOSIT OF THE MICROORGANISMS

*Aspergillus flavus,* designated NRRL 21882 and NRRL 21368; *A. parasiticus,* designated NRRL 21369; have been deposited under the provisions of the Budapest Treaty on Nov. 12, 1997 (NRRL 21882), Dec. 8, 1994 (NRRL 21368 and NRRL 21369) with the U.S.D.A. Agricultural Research Service Patent Culture Collection (National Center for Agricultural Utilization Research, 1815 N. University Street, Peoria, Ill., 61604). *Aspergillus oryzae* strain S-03, designated NRRL 30038, and *Aspergillus sojae* strain S-12 designated NRRL30039, have been deposited on Jul. 2, 1998 under the provisions of the Budapest Treaty with the U.S.D.A. Agricultural Research Service Patent Culture Collection (National Center for Agricultural Utilization Research, 1815 N. University Street, Peoria, Ill. 61604).

DETAILED DESCRIPTION OF THE INVENTION

The addition of highly competitive, non-toxigenic strains of *A. flavus, A. parasiticus, A. oryzae,* and *A. sojae* as well as mixtures of any of the strains, to soil results in lower concentrations of toxins in agricultural commodities. The non-toxigenic strains of Aspergillus become biocompetitive with the soil microflora and prevent buildup of toxin-producing strains that normally occurs during late-season drought. Through biocompetition, the toxigenic strains of fungi found naturally in soil are replaced by non-toxigenic strains added to the soil. Therefore, any crop subjected to late-season drought stress are invaded predominately by the biocompetitive strains which are unable to produce toxins.

The method of the invention is applicable to any agricultural commodity which is grown for human consumption and/or which is damaged by fungal toxins such as for example, peanuts, corn, cotton, etc.

For purposes of this invention, a fungal preparation or fungal agricultural biocontrol composition refers to a microbial preparation wherein the microbes comprise, consist essentially of, or consist of non-toxigenic strains of Aspergillus. The fungal preparations may contain one or more of non-toxigenic strains of Aspergillus. Non-toxigenic strains of Aspergillus include any strain which does not produce the toxins aflatoxin and cyclopiazonic acid (CPA). The agricultural biocontrol composition for purposes of this invention includes a non-toxigenic strain or strains of fungi on agriculturally acceptable carriers which may be any carrier which the fungi can be attached and are not harmful to the fungi or crops which are treated with the composition. Examples of non-toxigenic strains include *Aspergillus flavus, A. parasiticus, A. oryzae,* and *A. sojae.* The fungi especially useful in the present invention are strains possessing the identifying characteristics of non-toxigenic *Aspergillus flavus,* designated NRRL 21882 and NIRL 21368; non-toxigenic *A. parasiticus,* designated NRRL 21369; non-toxigenic *A. oryzae,* designated NRRL 447, NRRL 552, NRRL 451, NRRL 1730, and S-03; NRRL 30038 and non-toxigenic *A. sojae*, designated NRRL 3351, NRRL 1988, NRRL 5595, NRRL 5596, NRRL 6271, and S-12 NRRL 30039. These characteristics are the inability to produce the toxins aflatoxin and CPA and the ability to be biocompetitive when applied to soils growing agricultural commodities. *A. oryzae* and *A. sojae* are "koji molds" that are used in fermentation processes that result in the production of soy sauce and other products used for human consumption. Strains S-03 and S-12 (NRRL 30038 and 30039, respectively) were obtained commercially from a food manufacturer (Higuchi Natunosuke Shoten Co. LTD., 14-2 Harima-cho, Abeno-ku, Osaka, Japan 545).

Non-toxigenic strains of Aspergillus are cultured as single strains on granular food sources, such as for example rice, rye, etc.; or incorporated into extruded food matrices, such as for example wheat gluten-kaolin matrices. These food sources contain approximately $10^6$ colony forming units (CFU) of fungi per gram of food source. For granular food sources such as rice or rye, innoculated grains are incubated at about 30° C. for about 4 days, rotating at approximately 2 rev/minute while tilted at 70° from horizontal to gently agitate the grain and prevent fungal sporulation. The inoculated product is stored at about 5° C. until use. For food matrices, conidia are incorporated into the matrix, extruded, cut into lengths that can be easily applied with standard farm equipment and dried for storage at about 5° C.

The non-toxigenic strains of Aspergillus are applied to soil in amounts effective to reduce toxin levels in agricultural commodities. As used herein "reduce toxin levels" refers to a reduction in amounts of toxin compared to that which would be expected in agricultural commodities which were not treated according to the methods of the present invention. Any accurate method of measuring and comparing toxin levels may be used for such comparisons, as would be apparent to those skilled in the art. As used herein "in amounts effective", "an amount effective" or "an effective amount" refer to the amount of the fungal preparation administered wherein the effect of the administration acts to reduce toxin contamination of agricultural commodities. The granular or extruded products are applied to the soil at a rate of approximately 20 to 900 pounds per acre, with 100–200 pounds per acre preferred, and 20–50 pounds per acre most preferred, when the foliage canopy is about 12 inches wide. The soil surface under the canopy provides a humid, protected environment which promotes growth and sporulation of the non-toxigenic fungi. The strains can be applied as single strain compositions or the dried products can be mixed in about equal proportions to provide a composition made up of different strains of Aspergillus.

The following examples are intended to further illustrate the invention and are not intended to limit the scope of the invention as defined by the claims.

EXAMPLE 1

Strains of *A. flavus* were isolated from peanuts grown in the Environmental Control Plot Facility at the National Peanut Research Laboratory during crop year 1991. Randomly selected peanuts, which were grown under drought stress conditions conducive to invasion of peanuts with Aspergillus and contamination with aflatoxin, were surface sterilized with a 2.0% solution of sodium hypochlorite and incubated on Czapek agar plates at 25° C. for 7 days. Fungal colonies that grew from the peanuts were transferred to Czapek agar slants and identified as to genus and species. Numerous isolations of A. flavus and A. parasiticus were made. Strains were maintained on Czapek agar slants and as dry conidia on silica gel. In a screening program (see example 4 for details of the screening program) to identify non-toxigenic strains of A. flavus for possible use as biocontrol agents against aflatoxin contamination of peanuts, it was found that a particular strain of A. flavus (NPL 45; NRRL 21882) was not only incapable of producing aflatoxin, but also incapable of producing CPA, another mycotoxin commonly produced by A. flavus.

EXAMPLE 2

SCREENING FUNGAL ISOLATES FOR NON-TOXIGENIC STRAINS

A screening program was developed to identify non-toxigenic strains of A. flavus and A. parasiticus for possible use as biocontrol agents against aflatoxin contamination of peanuts. All fungi included in the screening program were cultured in vials for 4 days at 30° C. on a liquid medium containing glucose, soytone, yeast extract, and sucrose (Horn et al., Mycologia, Volume 88 (4), 574–587, 1996; herein incorporated by reference). Vial cultures were extracted by adding 1 mL of chloroform to each vial, breaking up the fungal material with a spatula, and vortexing for 30 sec. Vials were allowed to sit undisturbed for several minutes to allow the chloroform and aqueous layers to separate. Occasionally, centrifugation was required to achieve separation of the two layers. For aflatoxin analysis, an aliquot of the chloroform layer was transferred to a 4 mL HPLC autosampler vial, evaporated to dryness under a stream of nitrogen, and redissolved in HPLC injection solvent consisting of methanol:water:acetic acid (62:38:0.1, v/v/v). Aflatoxins were quantified by reversed-phase HPLC analysis with a Waters Nova-Pak $C_{18}$ column, a mobile phase of water:methanol:butanol (70:35:0.6,v/v/v), and fluorescence detection. Fluorescence of aflatoxins $B_1$ and $G_1$ was enhanced by postcolumn photochemical derivatization with a photochemical reactor (Joshua, Journal of Chromatography A, Volume 654, 247–254, 1993). For analysis of CPA and other aflatoxin biosynthetic pathway intermediates, another aliquot of the chloroform layer was transferred to a 4 mL vial, evaporated to dryness under a stream of nitrogen, and redissolved in HPLC mobile phase consisting of n-heptane:2-propanol:water:40% tetrabutylammonium hydroxide (2560:1120:32:8,v/v/v/v/). CPA and other metabolites were separated on a Zorbax Rx-Sil column and detected by photodiode array. Metabolite standards that cultures were screened against included CPA, O-methylsterigmatocystin, sterigmatocystin, norsolorinic acid, averufin, averantin, and kojic acid.

Aspergillus flavus strains NRRL 21882 (NPL 45), NaRL 21368 (AFCM), NRRL 18543 (AF36), P61, P84, and F48; A. parasiticus strain NRRL 21369 (CM2); A. oryzae NRRL 447, NRRL 552, NRRL 451, NRRL 1730, and NRRL 30038 (S-03) and A. sojae NRRL 3351, NRRL 1988, NRRL 5595, NRRL 5596, NRRL 6271, and NRRL (S-12) were cultured as described above and analyzed for production of aflatoxin, CPA, and other metabolites listed above. Strains P61, P84 and F48 are known aflatoxin and/or CPA producers and are routinely included in the screening process as positive controls.

Results of the analyses for some of the cultures for aflatoxin and CPA are shown in Table 1 below. Strain AF36 (NRRL 18543), as well as the three strains known to produce CPA, produced CPA. All strains produced kojic acid. No intermediates (containing the bis-furan ring system) in the aflatoxin biosynthetic pathway were detected in any of the isolates. Only trace amounts (<0.1 μg/ml) of aflatoxin production occurred with any of the NRRL isolates.

TABLE 1

| Biocompetitive Agent Metabolite Screen. CPA Production by Isolates of A. flavus | | |
|---|---|---|
| Strain | Aflatoxin (μg/ml) | CPA (μg/ml) |
| AFCM-NRRL 21368 | 0.002 | 0 |
| NPL45-NRRL 21882 | 0.019 | 0 |
| P 61 | 0.008 | 42.2 |
| P 84 | 0.066 | 46.1 |
| F 48 | 227.950 | 47.2 |
| AF 36-NRRL 18543 | 0.001 | 38.7 |

EXAMPLE 3

A. flavus, strain NRRL 21882 (NPL 45), was irradiated under ultraviolet light to produce color mutant strains that lack the capability of producing aflatoxins, CPA, or known toxic intermediates in the aflatoxin biosynthetic pathway. A color mutant was isolated (NRRL 21368) that was incapable of producing aflatoxins, CPA, or known toxic intermediates in the aflatoxin biosynthetic pathway.

A color mutant strain of A. parasiticus (NRRL 6111) that is a known producer of aflatoxins and an early biosynthetic precursor to aflatoxin, norsolorinic acid, was irradiated under ultraviolet light to produce other mutant strains that lack the capability of producing aflatoxins, CPA, or known toxic intermediates in the aflatoxin biosynthetic pathway. A color mutant was isolated (NRRL 21369) and found to be incapable of producing aflatoxins, norsolorinic acid, other known intermediates in the aflatoxin biosynthetic pathway, or CPA.

EXAMPLE 4

FIELD DELIVERY OF BIOCOMPETITIVE STRAINS

Rice inoculum was prepared by culturing each strain on autoclaved, long-grain rice in 2800-ml Fernbach flasks (500 g of rice with 150 ml distilled water). Rice was inoculated with 1 ml of a conidial suspension (106/ml) and incubated at 30° C. for 4 d on a rotating platform (2 rev/min) tilted 70° from horizontal to gently agitate the rice and prevent fungal sporulation. Rice inoculum was then dried in a shallow pan in a forced-air draft oven at 50° C. for 6 h or until the moisture content was ≦7%. Rice inoculum was stored at 5° C. until used.

Alternatively, inoculum in the form of pesta was prepared by the method of Connick et al. (Biological Control, Volume 1, 281–287,1991). Conidia of NRRL 21368 (A. flavus) and NRRL 21369 (A. parasiticus) were incorporated into a wheat gluten-kaolin matrix by extrusion. Extruded product (pesta) was cut into 1–2 mm lengths and dried for storage prior to use.

For field application, inoculum was placed in a Gandy box fitted to a tractor and banded over the peanut row, optimally at 40–50 days after planting, or when the width of a peanut row (measured from the outer edges of the foliage canopy) is about 12 inches. The inoculum filters through the canopy of foliage and comes to rest in a humid, protected environment on the soil surface under the canopy. Uptake of moisture by the inoculum granules results in growth of the incorporated biocompetitive fungi, which produces an abundance of conidia on the surface of the granules. As the conidia are dispersed over the soil surface, full delivery of the biocompetitive fungi is realized.

EXAMPLE 5

Biocompetitive agents, NRRL 21882 (*A. flavus,* NPL 45), NRRL 18991 (*A. parasiticus;* see U.S. Pat. No. 5,292,661—Mar. 8, 1994), NRRL 21368 (*A. flavus* color mutant of NRRL 21882), and NRRL 21369 (*A. parasiticus* color mutant), were tested in the NPRL environmental control plot facility for control of preharvest aflatoxin contamination of peanuts during crop year 1992. Plots consisted of six rows of cv. Florunner peanuts (6 m long spaced 0.9 m apart). Plots were inoculated with the biocompetitive agents by distributing fungus-colonized rice inoculum on soil around peanut plants at approximately 45 days after planting at a rate of 200 pounds per acre. Treatments consisted of NRRL 21882 alone, NRRL 18991 alone, NRRL 21882 and NRRL 18991 in combination, and a combination of NRRL 21368 and NRRL 21369. Equivalent plots were also left untreated to serve as controls. Harvested peanuts were shelled and kernels were sized into commercial categories including jumbo, medium, number 1, sound splits, and oil stock. Visibly moldy and damaged kernels were hand-picked from the jumbo, medium, number 1, and sound splits categories (edible categories) for analysis as a separate category. All peanuts were subjected to aflatoxin analysis with no subsampling using the high-performance liquid chromatography method of Dorner and Cole (J. Assoc. Off. Anal. Chem., Volume 71, 43–47, 1988; herein incorporated by reference).

Results of aflatoxin analyses of peanuts at harvest are shown below in Table 2. Aflatoxin concentrations for the combined edible (jumbo, medium, number 1, and sound splits), inedible (oil stock and damaged kernels), and total kernels categories were calculated by dividing the total weight of toxin (ng) for the combined categories by the total peanut weight (g) for those combined categories. Reductions in aflatoxin contamination as a result of treatment with the biocompetitive agents ranged from 39.2% in inedible category peanuts from the treatment with the combination of *A. flavus* and *A. parasiticus* color mutants (NRRL 21368+NRRL 21369) to 98.9% in edible category peanuts from the treatment with the combination of wild-type isolates of *A. flavus* and *A. parasiticus* (NRRL 21882+NRRL 18991). A higher degree of control was usually seen in the more important edible category peanuts with the exception of the treatment with *A. parasiticus* NRRL 18991 alone.

TABLE 2

Aflatoxin contamination (ppb) of peanuts treated with various combinations of biocompetitive agents during crop year 1992.

| | Peanut Category | | |
|---|---|---|---|
| Treatment | Edible | Inedible | Total |
| Control | 171.1 | 2188.2 | 354.9 |
| NRRL 21882 | 9.7 | 685.1 | 71.2 |
| % Reduction | 94.3% | 68.7% | 79.9% |

TABLE 2-continued

Aflatoxin contamination (ppb) of peanuts treated with various combinations of biocompetitive agents during crop year 1992.

| | Peanut Category | | |
|---|---|---|---|
| Treatment | Edible | Inedible | Total |
| Control | 278.7 | 5901.4 | 579.5 |
| NRRL 18991 | 76.4 | 434.1 | 108.1 |
| % Reduction | 72.6% | 92.6% | 81.3% |
| Control | 75.1 | 6465.9 | 525.2 |
| NRRL 21882 + 18991 | 0.8 | 273.7 | 44.3 |
| % Reduction | 98.9% | 95.8% | 91.5% |
| Control | 147.4 | 2072.3 | 407.4 |
| NRRL 21368 + 21369 | 26.8 | 1260.8 | 151.0 |
| % Reduction | 81.8% | 39.2% | 62.9% |

EXAMPLE 6

In crop year 1993, a study similar to that described in Example 5 was carried out except that treatment with the individual strains, NRRL 21882 and NRRL 18991, was not done. Treatments included the combination of NRRL 21882 plus NRRL 18991 and NRRL 21368 plus NRRL 21369. Results, shown below in Table 3, again showed better control in the edible category peanuts and better overall control by the wild-type isolates (NRRL 21882 plus NRRL 18991).

TABLE 3

Aflatoxin contamination (ppb) of peanuts treated with various combinations of biocompetitive agents during crop year 1993.

| | Peanut Category | | |
|---|---|---|---|
| Treatment | Edible | Inedible | Total |
| Control | 89.5 | 3102.7 | 361.8 |
| NRRL 21882 + 18991 | 3.2 | 449.1 | 49.2 |
| % Reduction | 96.5% | 85.5% | 86.4% |
| Control | 100.1 | 1192.0 | 242.9 |
| NRRL 21368 + 21369 | 5.3 | 603.6 | 84.1 |
| % Reduction | 94.7% | 49.4% | 65.4% |

EXAMPLE 7

Biocompetitive agents, NRRL 21882 (*A. flavus*, NPL 45) and NRRL 18543 (*A. flavus*, AF36), were field-tested for control of preharvest aflatoxin and CPA contamination of peanuts. Plots (15 m×6 rows, spaced 0.9 m apart) of cv. Florunner peanuts were grown in an agricultural field in Terrell County, Georgia, during crop years 1996 and 1997. Plots were inoculated with the biocompetitive agents by distributing fungus-colonized rice inoculum on soil around peanut plants at approximately 45 days after planting at a rate of 200 pounds per acre in 1996 and 20 pounds per acre in 1997. Four plots were separately treated with each biocompetitive strain alone and four untreated plots served as controls. Plots that were treated with a particular biocompetitive fungus in 1996 were treated with the same biocompetitive fungus in 1997.

Peanuts were harvested with conventional peanut-harvesting equipment. Peanuts were shelled and kernels were sized into commercial categories including jumbo, medium, number 1, sound splits, and oil stock. Visibly moldy and damaged kernels were hand-picked from the jumbo, medium, number 1, and sound splits categories (edible categories) for analysis as a separate category. Each size category (including damaged) was analyzed for aflatoxin and CPA. Peanuts were prepared for analysis by grinding to a paste in a vertical cutter mixer. Aflatoxin analyses were carried out on 200 g of the ground paste using the HPLC method cited in Example 5. CPA analyses were carried out on 50 g of ground paste by extraction with methanol:1% sodium bicarbonate (70:30, v/v). The extract was filtered and purified on a CPA-immunoaffinity column. Eluate from the column was subjected to HPLC analysis using the system described in Example 2 above for fungal cultures. After aflatoxin and CPA concentrations were determined for each category, concentrations for edible peanuts (jumbo, medium, and number 1 categories) and all peanuts (all categories) were calculated by dividing the total weight of toxin (ng) for the combined categories by the total peanut weight (g) for those combined categories.

Results for edible category peanuts and all peanuts combined are shown below in Table 4. The treatment of peanut soil with NPL 45 (NRRL 21882) resulted in a mean reduction in aflatoxin of edible peanuts of 79.5%, whereas treatment with AF36 (NRRL 18543) resulted in a mean reduction of 61.4%. The reduction in all peanuts averaged 27.2% for treatment with NPL 45 and 26.3% for treatment with AF36. CPA contamination of peanuts in control plots was relatively low under these conditions, but treatment with NPL 45 resulted in no contamination of edible peanuts with CPA and a 39% reduction in CPA levels in all peanuts. In contrast, treatment with the CPA-producing fungus, AF36, resulted in large increases in CPA contamination in both edible peanuts as well as all peanuts.

TABLE 4

Aflatoxin and Cyclopiazonic Acid in Peanuts.

| Treatment | | Edible Peanuts | | All Peanuts | |
|---|---|---|---|---|---|
| | | Aflatoxin | CPA | Aflatoxin | CPA |
| Control | 1 | 8.4 | 0.0 | 195.3 | 18.2 |
| | 2 | 44.0 | 3.7 | 44.8 | 3.1 |
| | 3 | 5.0 | 3.1 | 18.9 | 6.4 |
| | 4 | 27.7 | 0.0 | 156.4 | 8.9 |
| | Mean | 21.5 | 1.7 | 103.9 | 8.7 |
| NPL45 | 1 | 1.4 | 0.0 | 155.4 | 9.7 |
| | 2 | 7.5 | 0.0 | 124.1 | 7.0 |
| | 3 | 0.0 | 0.0 | 2.2 | 0.0 |
| | 4 | 8.6 | 0.0 | 20.8 | 4.3 |
| | Mean | 4.4 | 0.0 | 75.6 | 5.3 |
| AF 36 | 1 | 0.5 | 191.4 | 35.3 | 760.2 |
| | 2 | 11.5 | 18.5 | 160.3 | 100.2 |
| | 3 | 21.1 | 0.0 | 90.5 | 82.6 |
| | 4 | 0.1 | 69.2 | 20.2 | 344.3 |
| | Mean | 8.3 | 69.8 | 76.6 | 321.9 |

EXAMPLE 8

Biocompetitive agents NRRL 21882 (*A. flavus*), NRRL 21368 (*A. flavus*), and NRRL 21369 (*A. parasiticus*) were field-tested for control of aflatoxin and CPA contamination over the course of a three-year period (1995–1997). In 1995 soil was inoculated with 200 pounds per acre of rye seed that had been colonized with NRRL 21368 and NRRL 21369. In 1996 soil inoculum in the form of pesta included a combination of NRRL 21368 (*A. flavus*), and NRRL 21369 (*A. parasiticus*) applied at a rate of 200 pounds per acre to 1.5 acres of peanuts. An equivalent area of peanuts was not treated and served as controls. In 1997 the testing was continued by treating the same soil with a mixture of NRRL 21882 (*A. flavus*) and NRRL 21369 (*A. parasiticus*). In 1995 and 1996, environmental conditions were not conducive for preharvest aflatoxin contamination, and peanuts (both from treated and control plots) were not contaminated. However, in 1997 a significant drought occurred near the end of the growing season, thus providing conditions that were conducive for contamination to occur. Peanuts were harvested with conventional equipment and placed in conventional peanut drying wagons for transport to a Federal-State Inspection Service sampling station. A pneumatic probe was used to draw 15 samples from each wagon containing peanuts from the treated and untreated areas. The samples were composited by the automatic sampler, and they were taken to the laboratory where they were riffle-divided into eight separate samples. Each sample was shelled and sized into commercial size categories as described in Example 5 with damaged kernels being removed from the edible categories. All peanuts from each category were extracted and analyzed for aflatoxin. Subsequently, another eight samples were taken from each group of treated and untreated peanuts and analyzed for CPA. Concentrations of aflatoxin and CPA for all peanuts were calculated as in Example 5 by dividing the total weight of toxin (ng) for the combined categories by the total peanut weight (g) for those combined categories.

Results are presented below in Table 5. The average reduction in aflatoxin in treated peanuts compared to controls was 91.6%, and the average reduction in CPA in treated peanuts compared to controls was 85.7%.

TABLE 5

Aflatoxin and CPA contamination (ppb) of field-grown peanuts in 1997 and treated with a combination of biocompetitive agents including NRRL 21882 (*A. flavus*) and NRRL 21369 (*A. parasiticus* color mutant).

| | Aflatoxin | CPA |
|---|---|---|
| Control | 603.5 | 30.7 |
| Treated | 50.8 | 4.4 |
| % Reduction | 91.6% | 85.7% |

EXAMPLE 9

AFLATOXIN REDUCTION IN CORN

Soil in eight corn plots (5.5×24.4 m) was inoculated with formulations including NRRL 21368 (*A. flavus*), and NRRL 21369 (*A. parasiticus*) during crop years 1994–1996. In 1997 the same plots were inoculated with NRRL 21882 (*A. flavus*) and NRRL 21369 (*A. parasiticus*). Eight corn plots in a separate part of the field were not inoculated and served as controls. Corn from each plot was harvested with a conventional combine and bagged. Corn was ground with a Romer subsampling mill and analyzed for aflatoxin by HPLC as cited in Example 5.

In 1994 and 1995, aflatoxin contamination did not occur to any significant degree, probably because environmental conditions in those years were relatively cool and wet. In 1996, the aflatoxin concentration in corn from treated plots averaged 23.6 ppb, a significant reduction (P<0.001) compared with the aflatoxin in control plots, which averaged 188.3 ppb. This coincided with a significantly (P=0.018) reduced colonization of corn by wild-type *A. flavus* in treated plots (1.8% of kernels) compared with control plots (5.4%). In 1997, aflatoxin was again significantly reduced (P=0.024) in treated corn (29.8 ppb) compared with untreated corn (87.5 ppb). Treated corn was predominately colonized by the introduced strain of *A. flavus* (NRRL 21882)(26.7% of kernels) compared with wild-type *A. flavus* (2.9%).

EXAMPLE 10

AFLATOXIN REDUCTION BY *ASPERGILLUS ORYZAE* AND *ASPERGILLUS SOJAE*

*Aspergillus oryzae* and *A. sojae* are species that are closely related to *A. flavus* and *A. parasiticus*. Several strains of these fungi were cultured on rice as in Example 5 and tested in environmental control plots (Example 5) for biological control of aflatoxin contamination. Strains of *A. oryzae* tested included NRRL 447, NRRL 552, NRRL 451 and NRRL 1730. Strains of *A. sojae*, tested were NRRL 3351, NRRL 1988, NRRL 5595, NRRL 5596 and NRRL 6271. Each strain was cultured separately and the rice cultures were mixed in approximately equal amounts based on weight before application to the soil. Strain NRRL 451 was mixed in at half the weight of the other strains. The mixture was applied at a rate of 960 lbs./acre on two plots (See Example 5). Two untreated plots served as controls.

Results of aflatoxin analyses of peanuts at harvest are shown below in Table 6. Mixtures of *A. oryzae* and *A. sojae* reduced the concentration of aflatoxin, particularly in the edible category peanuts.

TABLE 6

| | Peanut Category | | |
|---|---|---|---|
| Treatment | Edible | Inedible | Total |
| Control | 640.3 | 9709.5 | 1472.4 |
| A. oryzae/A. sojae | 9.7 | 3167.6 | 234.0 |
| % Reduction | 98.5 | 67.4 | 84.1 |

The foregoing detailed description is for the purpose of illustration. Such detail is solely for that purpose and those skilled in the art can make variations therein without departing from the spirit and scope of the invention.

We claim:

1. A non-toxigenic fungal biocontrol agent comprising a biologically pure Aspergillus strain selected from the group consisting of *Aspergillus oryzes, Aspergillus sojae* and mixtures thereof; wherein said strain does not produce aflatoxin, any bis-furan ring-containing intermediates in the aflatoxin biosynthetic pathway, and cyclopiazonic acid.

2. An agricultural biocontrol composition comprising a biologically pure non-toxigenic strain of Aspergillus selected from the group consisting of *Aspergillus oryzae, Aspergillus sojae* and mixtures thereof; wherein said strain does not produce aflatoxin, any bis-furan ring-containing intermediates in the aflatoxin biosynthetic pathway, and cyclopiazonic acid, and an agriculturally acceptable carrier.

3. A non-toxigenic fungal biocontrol agent consisting essentially of a biologically pure Aspergillus strain having all of the identifying characteristics of a strain selected from the group consisting of NRRL 21368, NRRL 2136g, NRRL 21882, NRRL 30038, NRRL 30039, and mixtures thereof.

4. An agricultural biocontrol composition consisting essentially of a biologically pure Aspergillus strain having all of the identifying characteristics of a strain selected from the group consisting of NRRL 21368, NRRL 21369, NRRL 21882, NRRL 30038, NRRL 30039, and mixtures thereof; and an agriculturally acceptable carrier.

5. A method for reducing toxin contamination of agricultural commodities comprising applying an agricultural biocontrol composition containing a biologically pure strain of Aspergillus having all of the identifying characteristics of an Aspergillus strain selected from the group consisting of NRRL 21368, NRRL 21369, NRRL 21882, NRRL 30038, NRRL 30039, and mixtures thereof with an agriculturally acceptable carrier; to soil around plants, wherein said Aspergillus strain does not produce aflatoxin, any bis-furan ring-containing intermediates of the aflatoxin biosynthetic pathway, and cyclopiazonic acid.

6. The method of claim 5 wherein said agricultural commodities are selected from the group consisting of peanuts, corn, cotton, and tree nuts.

7. A method for reducing toxin contamination of agricultural commodities comprising applying an agricultural biocontrol composition containing a biologically pure Aspergillus strain selected from the group consisting of *Aspergillus oryzae, Aspergillus sojae*, and mixtures thereof; with an agriculturally acceptable carrier; to soil around plants, wherein said Aspergillus strain does not produce aflatoxin, any bis-furan ring-containing intermediates of the aflatoxin biosynthetic pathway, and cyclopiazonic acid.

8. The method of claim 7 wherein said agricultural commodities are selected from the group consisting of peanuts, corn, cotton, and tree nuts.

* * * * *

UNITED STATES PATENT AND TRADEMARK OFFICE
CERTIFICATE OF CORRECTION

PATENT NO.   : 6,027,724
DATED        : February 22, 2000
INVENTOR(S)  : Joe W. Dorner, Bruce W. Horn and Richard J. Cole It is certified that error appears in the above-identified patent and that said Letters Patent is hereby corrected as shown below:

Claim 1,
Line 3, please change "oRYZES" to read -- oRYZAE --

Claim 3,
Line 4, "NRRL 2136g" should read -- NRRL 21369 --

Signed and Sealed this

Second Day of April, 2002

Attest:

Attesting Officer

JAMES E. ROGAN
Director of the United States Patent and Trademark Office